(12) United States Patent
Deghenghi et al.

(10) Patent No.: US 7,098,305 B2
(45) Date of Patent: Aug. 29, 2006

(54) SUSTAINED RELEASE OF MICROCRYSTALLINE PEPTIDE SUSPENSIONS

(75) Inventors: Romano Deghenghi, St. Cergue (CH); Francois Boutignon, Ermont (FR)

(73) Assignee: Ardana Bioscience Limited, Edinburgh (GB)

( * ) Notice: Subject to any disclaimer, the term of this patent is extended or adjusted under 35 U.S.C. 154(b) by 414 days.

(21) Appl. No.: 10/080,130

(22) Filed: Feb. 19, 2002

(65) Prior Publication Data

US 2003/0044463 A1   Mar. 6, 2003

(51) Int. Cl.
A61K 38/00 (2006.01)
A61K 38/04 (2006.01)
C07K 5/00 (2006.01)
C07K 7/00 (2006.01)
C07K 16/00 (2006.01)

(52) U.S. Cl. .................... 530/326; 530/345; 514/14

(58) Field of Classification Search ............ 424/489, 424/499; 514/2
See application file for complete search history.

(56) References Cited

U.S. PATENT DOCUMENTS 4,256,737 A    3/1981  Nestor et al. ............... 424/177
5,648,096 A *  7/1997  Gander et al. ............... 424/489
5,773,032 A    6/1998  Engel et al. ................. 424/501
6,258,933 B1 * 7/2001  Gunther et al. ............. 530/344
2002/0198146 A1* 12/2002 Damm et al. ................. 514/12

FOREIGN PATENT DOCUMENTS

GB    2 052 258 A     1/1981
WO    WO 95/15767     6/1995
WO    98/25642        6/1998
WO    00/47234        8/2000
WO    WO 00/47234  *  8/2000

OTHER PUBLICATIONS

Martindale, the Complete Drug Reference, pp. 322-330, "Insulin" (K. Parfitt, ed., 32nd ed. 1999).

* cited by examiner

Primary Examiner—Michael P. Woodward
Assistant Examiner—David Vanik
(74) Attorney, Agent, or Firm—Winston & Strawn LLP

(57) ABSTRACT

The invention relates to a method of preventing gel formation of a hydrophobic peptides by contacting the hydrophobic peptide with a counter-ion in an amount and at a molar ratio with the peptide that are sufficient to provide a fluid, milky microcrystalline aqueous suspension of the peptide without formation of a gel. The invention also relates to a fluid, milky microcrystalline aqueous suspension of a hydrophobic peptide and a counter-ion in water, wherein the peptide and counter-ion are present in amounts and at a molar ratio sufficient to form, upon mixing, the suspension without formation of a gel.

14 Claims, 1 Drawing Sheet

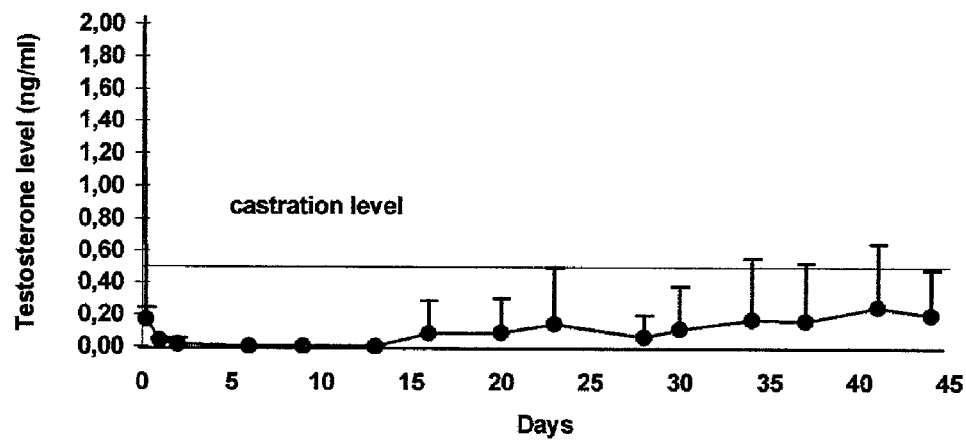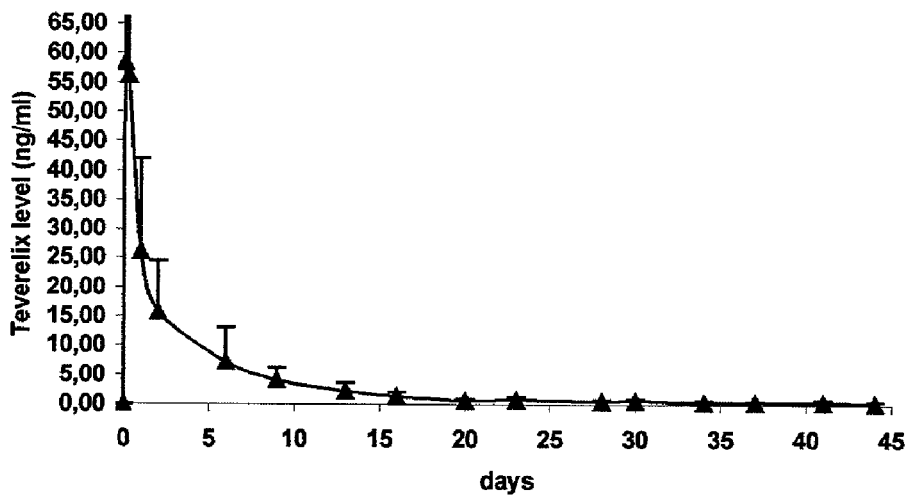

SUSTAINED RELEASE OF MICROCRYSTALLINE PEPTIDE SUSPENSIONS

BACKGROUND OF THE INVENTION

There is frequently a need to deliver biologically active peptides to animals and humans in formulations providing a sustained release of the active principle. Such formulations may be provided by incorporating the active principle in biodegradable and biocompatible polymers in form of microcapsules, microgranules or implantable rods, or alternatively using mechanical devices such as micropumps or non-biodegradable containers. If the peptide is highly soluble in aqueous media, it can be formulated as a complex with non-degradable polymers such as cellulose derivatives, or mixed with polymer solutions, which form a gel upon parenteral injection, from which the active peptide is slowly released.

All the above-mentioned formulations have drawbacks and limitations, such as the large volume of suspending fluids or the need to remove the non-degradable device. In the case of gel forming peptides, there is frequently a problem of bioavailability, which interferes with the desired sustained action of the active principle.

Some of the problems due to physico-chemical aspects of peptides have been described in article by R. Deghenghi "Antarelix" in Treatment with GnRH Analogs: Controversies and Perspectives", edited by M. Filicori and C. Flamigni, The Parthenon Publishing Group, New York and London 1996, pages 89–91. Additional problems were illustrated by J. Rivier "GnRH analogues towards the next millennium" in GnRH Analogues, edited by B. Lunenfeld, The Parthenon Publishing Group, New York and London 1999, pages 31–45 and by other workers such as M. F. Powell et al. "Parenteral Peptide Formulations: Chemical and Physical Properties of Native LHRH and Hydrophobic Analogues in Aqueous Solution" in Pharmaceutical Research, Vol. 8, 1258–1263 (1991).

Accordingly, there is a need for new formulations and methods of administration that avoid these problems, and this need is addressed by the present invention.

SUMMARY OF THE INVENTION

The invention relates to a method of preparing a sustained release formulation of a peptide or peptidomimetic. This method advantageously comprises associating or contacting the peptide or peptidomimetic with a counter-ion in an amount and at a molar ratio that are sufficient to provide a fluid, milky microcrystalline aqueous suspension without formation of a gel.

The invention also relates to a fluid, milky microcrystalline aqueous suspension of a peptide or peptidomimetic and a counter-ion in water, wherein the peptide and counter-ion are present in amounts and at a molar ratio sufficient to form, upon mixing, the suspension without formation of a gel.

The avoidance of a gel enables an injectable suspension to be formulated. When these aqueous suspensions are injected parenterally (i.e., subcutaneously or intramuscularly) into a mammal, such as a human, a sustained release of the peptide over time is obtained. Generally, this sustained release lasts at least about 2 weeks to one month or even to about 45 days or longer.

Preferably, the counter-ion is a salt of a strong proton donor. Most preferred counter-ions are strong acids such as trifluoro methanesulfonic acid, benzenesulfonic acid, trifluoroacetic acid or sulfuric acid. The peptide may be a somatostatin analogue, such as Vapreotide, Octreotide, Lanreotide or SOM-230. Also, the peptide may be a GnRH analogue, and preferably is a GnRH antagonist. More preferred GnRH antagonists include Azaline B, Abarelix, Antide, Ganirelix, Cetrorelix, or FE200486. These peptides are preferably present in the suspension in the form of their acid salts, e.g., sulfonate, trifluoroacetate or sulfate salts. Ac-D-Nal-D-Cpa-D-Pal-Ser-Tyr-D-Hci-Leu-Ilys-Pro-D-Ala-NH$_2$ trifluoroacetate and Ac-D-Nal-D-Cpa-D-Pal-Ser-Tyr-D-Hci-Leu-Ilys-Pro-D-Ala-NH$_2$ sulfate are the most preferred compounds.

The peptide or peptidomimetic preferably forms a salt with the counter-ion, and the salt is preferably suspended in the aqueous medium at a concentration of at least 25 mg/ml and has a molar ratio of at least 1.6:1 of counter-ion:peptide. The salt is at least partially in the form of microcrystals having a particle size of between about 1 and 150 µm.

If desired, the aqueous suspension can contain an isotonic agent, such as mannitol. Also, the aqueous suspension may contain a pharmaceutically acceptable excipient. Advantageously, the suspension is dried to a lyophilized state which can be reconstituted by mixing with water or a buffer solution. Lyophilized compositions comprising these dried suspensions, as well as the methods for making the dried suspensions and reconstituting them as aqueous suspensions, represent additional embodiments of the invention.

BRIEF DESCRIPTION OF THE DRAWINGS

FIG. 1 is a graph which illustrates the pharmacodynamic effect (testosterone suppression) obtained by subcutaneous injection in rats of a suspension of Teverelix trifluoroacetate according to the invention; and FIG. 2 is a graph which illustrates the sustained release of the peptide Teverelix. for several weeks in rats injected with the suspension of Teverelix trifluoroacetate according to the invention.

DETAILED DESCRIPTION OF THE PREFERRED EMBODIMENTS

The present invention is directed to the unexpected discovery that certain peptides can be prepared or associated with various counter-ions and simply formulated to provide desirable suspensions of the peptide, which suspensions are highly useful for administering the suspension by injection. In particular, a fluid, milky, stable microcrystalline suspension of the peptide is obtained without formation of a gel that would interfere with the handling of the suspension or the bioavailability of the peptide after injection.

The peptide that is to be utilized in the present suspension can be any one of a variety of well known bioactive peptides or peptide analogues which mimic such peptides. Advantageously, these peptides are formulated to obtain a delayed and sustained release of the peptide after injection. While any peptide can be utilized in this invention, those peptides or peptidomimetics having between 3 and 45 amino acids have been found to be the most suitable. In particular, representative peptides or peptidomimetics are well known to those of ordinary skill in the art and need not be exhaustively mentioned here. Typical examples include GnRH analogues and antagonists, as well as somatostatin and analogues thereof. Specific peptides include Azaline B, Abarelix, Antide, Ganirelix, Cetrorelix, FE 200486, Vapreotides, Octreotide, Lanreotide and SOM-230. These peptides have between 6 and 12 amino acids and are synthetically made to mimic the biological activity of GnRH or somatostatin. The examples mention further preferred peptides.

It has been found that certain counter-ions are highly preferred for obtaining sustained release of the peptide. Suitable counter-ions are those which are strong proton donors. While many compounds are well known to provide this function, the most preferred are strong acids. Sulfuric acid, a well known commodity, is quite useful for this purpose, as are other strong inorganic acids. Sulfuric is preferred due to its ready formation of suitable sulfate salts with the peptides of the invention. Strong organic acids can also be used as counter-ions. These acids include sulfonic acids, such as trifluoro methane sulfonic acid and benzene sulfonic acid. Others, such as trifluoro acetic acid or other fluorinated acids can be used if desired.

The amount of counter-ion is preferably that which is in excess of what is necessary to form a stoichiometric salt of the peptide. The amount of counter-ion is typically at least 1.6 mol acid/mole peptide and preferably 2 mol/mol or greater. While no upper limit has been determined, the amount can be as high as 10 mol/mol. In addition, the injectable suspension should be concentrated to obtained the most desirable release profiles. By concentrated, we mean that the amount of peptide should be above 2.5% by weight of the overall formulation. This is conveniently achieved by adding to water or a buffer solution at least 25 mg/ml of the peptide. Amounts of as high as 100 mg/ml can be used, and these suspensions can also contain other additives. In addition to conventional pharmaceutically acceptable excipients, an isotonic agent, such as mannitol, can be included for its known purpose. Other usual pharmaceutical additives can be included, as desired.

The suspensions can be dried by freeze-drying or spray drying to form lyophilized compositions that can be stored as is and later reconstituted with sterile water or buffer solutions when an injectable formulation is to be prepared. These lyophilized compositions can be stored for relatively long periods of time prior to use. Also they can be easily sterilized and handled until the time when they are to be reconstituted.

An additional advantage of this discovery is the small volume of such suspensions, allowing parenteral injections through a fine needle and thus improving the local tolerance of the injected material. Furthermore, the material can also be used for the local treatment of diseased tissues, e.g., brachytherapy. The peptide is partially or totally in the microcrystalline form having a particle size of between about 1 and 150 µm, and preferably between about 5 and 25 µm. These small particles easily pass through the injection needle. In such injections, the amount of peptide ranges from about 0.1 to 5 mg per kg body weight of the mammal or human to which the suspension is to be administered.

A specific discovery was that a highly concentrated aqueous suspension of the peptide of the formula Ac-D-Nal-D-pClPhe-D-Pal-S-er-Tyr-D-Hci-LeuLys(iPr)-Pro-D-Ala-NH$_2$ Teverelix, a GnRH antagonist) as a trifluoroacetate (TFA) or sulfate salt does not, as might be expected by its hydrophobic character, form a gel but instead forms a microcrystalline milky suspension which is easy to inject parenterally in animals or humans, and which releases the active principle over several weeks (see FIGS. 1 and 2). Such behavior is not elicited by other salts such as the acetate, which result in the expected, but unwanted, formation of gels with poor bioavailability in vivo.

The invention thus represents a simple and elegant solution to the problem of how to suppress gelation of peptide salts while obtaining a prolonged sustained delivery of peptides in the form of highly concentrated suspensions.

EXAMPLES

Example 1

200 µL of 5% mannitol were added to approximately 15 mg of the LHRH antagonist Teverelix trifluoroacetate. The mixture was stirred using vortex during one minute and a flowing milky pearly suspension was obtained. The suspension is made of microcrystals of about 10 µm length. Microcrystals may clump together to form urchin like structures. The suspension was injected in rats (1 mg) subcutaneously and provided the pharmacodynamic effect of testosterone suppression for more than 45 days (FIG. 1). The pharmacokinetic analysis showed a sustained release of the peptide for several weeks (FIG. 2).

Example 2

200 µL of water were added to approximately 15 mg of the LHRH antagonist Teverelix trifluoroacetate. The mixture was stirred using vortex during one minute and a flowing milky pearly suspension was obtained.

Example 3

200 µL of water were added to approximately 15 mg of the LHRH antagonist Teverelix acetate. The mixture was stirred using vortex during one minute and a transparent gel was obtained. The addition of 20 µL of TFA (3 mols/mol) to the gel resulted in the formation of a fluid, flowing milky pearly suspension.

Example 4

200 µL of 100 mM TFA were added to approximately 15 mg of the LHRH antagonist Teverelix acetate (2 mols/mol) to obtain a flowing milky suspension. In addition, mixing 200 µL of 75 mM TFA with approximately 15 mg of the LHRH antagonist Teverelix acetate (1.5 mol/mol) resulted in a transparent gel being obtained after mixing. In another study, 100 µL of TFA of various concentrations were added to 7.5 mg of the LHRH antagonist Teverelix acetate, with the TFA/Teverelix molar ratio ranging from 1 to 3. A flowing milky suspension was obtained with molar ratios of 1.6, whereas gels were obtained at other molar ratios.

Example 5

200 µL of 150 mM TFA were added to amounts of the LHRH antagonist Teverelix acetate ranging from 5 to 30 mg (concentration ranging from 25 to 150 mg/ml). A flowing milky suspension was obtained with concentrations up to 100 mg/ml.

Example 6

200 µL of 150 mM TFA were added to approximately 15 mg of the LHRH antagonist Teverelix acetate (3 mols/mol) and a flowing milky suspension was obtained after mixing. The suspension was freeze-dried over-night. 200 µL of water or 5% mannitol were added to the lyophilisate and a flowing milky suspension was obtained after mixing and reconstitution.

Example 7

1 mL of 150 mM TFA were added to approximately 75 mg of the LHRH antagonist Teverelix acetate (3 mols/mol) and a flowing milky suspension was obtained after mixing. The suspension was freeze-dried over-night. 1 mL of water and 0.2M acetate buffer pH 4.0 were added to the lyophilisate and a flowing milky suspension was obtained after mixing and reconstitution. These suspensions were stable for at least 3 days at room temperature.

Example 8

100 µL of a 250 mM $H_2SO_4$ were added to 7.5 mg of the LHRH antagonist Teverelix acetate (5 mols/mol) and a flowing milky suspension was obtained after several hours. The suspension is made of microcrystals of about 100 µm length. Microcrystals may assemble together to form urchin like structures. The suspension was freeze-dried over-night. 100 µL of water or 5% mannitol were added to the lyophilisate and a flowing milky suspension was obtained after mixing and reconstitution.

Example 9

100 µL of a 150 mM trifluoromethane sulfonic acid solution were added to 7.5 mg of Teverelix acetate to obtain a free flowing milky suspension after mixing.

Example 10

100 µL of a 150 mM solution of benzenesulfonic acid were added to 7.5 mg Teverelix hydrochloride to give after a mixing a free flowing suspension.

Example 11

100 µL of a 200 mM solution of trifluoroacetic acid solution were added to 2.5 mg of Cetrorelix acetate to obtain a milky free flowing suspension.

Example 12

Free flowing suspensions were obtained by adding 100 µL of a 150 mM trifluoroacetic acid solution to 7.5 mg each of the following somatostatin analogues:
D-Phe-c[Cys-Tyr-D-Trp-Lys-Val-Cys]-Trp-$NH_2$
D-2Me-Trp-c[Cys-Phe-D-Trp-Lys-Thr-Cys]-Trp(2Me)-$NH_2$
D-Nal-c [Cys-Tyr-T-D-Tp-Lys-Val-Cys]-Trp(2Me)-$NH_2$
D-Phe-c[Cys-Tyr-D-Trp-Lys-Val-Cys]-Trp(2Me)-$NH_2$

Example 13

100 µL of a 5% mannitol—water solution were added to approximately 5 mg of the somatostatin analog known under the designation SOM 230, i.e., ETD-carboxy-c[Hyp-Phg-D-Trp-Lys-Tyr(Bzl)-Phe], as the trifluoroacetate salt. A milky free flowing suspension was thus obtained.

What is claimed is:

1. A fluid, milky microcrystalline aqueous suspension comprising Ac-D-Nal-D-Cpa-D-Pal-Ser-Tyr-D-Hci-Leu-Ilys-Pro-D-Ala-$NH_2$.trifluoroacetate and an isotonic agent.

2. The suspension of claim 1, wherein the amount of Ac-D-Nal-D-Cpa-D-Pal-Ser-Tyr-D-Hci-Leu-Ilys-Pro-D-Ala-$NH_2$.trifluoracetate ranges from about 0.1 to 5 mg per kg body weight of a mammal or human to which the suspension is to be administered.

3. The suspension of claim 1, which provides, when administered to a subject, a sustained release of peptide in vivo.

4. The suspension of claim 3, wherein the sustained release is over a period of two weeks.

5. The suspension of claim 1, wherein Ac-D-Nal-D-Cpa-D-Pal-Ser-Tyr-D-Hci-Leu-Ilys-Pro-D-Ala-$NH_2$.trifluoroacetate is suspended in an aqueous medium at a concentration of equal to or greater than 25 mg/mL.

6. The suspension of claim 1, wherein the isotonic agent is mannitol.

7. The suspension of claim 1, further comprising a pharmaceutically acceptable excipient.

8. The suspension of claim 1, wherein microcrystals are in the form of needles having a particle size of between 1 and 150 µm.

9. A method of preparing the suspension of claim 1 comprising, associating Ac-D-Nal-D-Cpa-D-Pal-Ser-Tyr-D-Hci-Leu-Ilys-Pro-D-Ala-$NH_2$ with trifluoroacetate counter-ion in an amount and at a molar ratio that are sufficient to provide a fluid, milky microcrystalline aqueous suspension without formation of a gel.

10. A method of preparing a lyophilized composition comprising Ac-D-Nal-D-Cpa-D-Pal-Ser-Tyr-D-Hci-Leu-Ilys-Pro-D-Ala-$NH_2$.trifluoroacetate comprising, lyophilizing the suspension of claim 1.

11. A method of preparing the suspension of claim 1 comprising, associating Ac-D-Nal-D-Cpa-D-Pal-Ser-Tyr-D-Hci-Leu-Ilys-Pro-D-Ala-$NH_2$ with trifluoroacetate counter-ion in an amount and at a molar ratio that are sufficient to provide a fluid, milky microcrystalline aqueous suspension without formation of a gel; lyophilizing to form a lyophilized composition; and adding water or buffer with mixing.

12. A method of preparing a sustained release formulation of Ac-D-Nal-D-Cpa-D-Pal-Ser-Tyr-D-Hci-Leu-Ilys-Pro-D-Ala-$NH_2$.trifluoroacetate comprising, associating Ac-D-Nal-D-Cpa-D-Pal-Ser-Tyr-D-Hci-Leu-Ilys-Pro-D-Ala-$NH_2$ with the trifluoroacetate counter-ion in an amount and at a molar ratio that are sufficient to provide the fluid, milky microcrystalline aqueous suspension of claim 1, such that, when administered to a subject, the peptide is released in vivo over a period of at least two weeks.

13. The method of claim 12, wherein the aqueous suspension is injected parenterally into a mammal or human subject to obtain a sustained release of Ac-D-Nal-D-Cpa-D-Pal-Ser-Tyr-D-Hci-Leu-Ilys-Pro-D-Ala-$NH_2$.trifluoroacetate for at least one month to about 45 days.

14. The method of claim 12, wherein the amount of Ac-D-Nal-D-Cpa-D-Pal-Ser-Tyr-D-Hci-Leu-Ilys-Pro-D-Ala-$NH_2$.trifluoroacetate in the suspension to be injected ranges from about 0.1 to 5 mg per kg body weight of the mammal or human subject.

* * * * *

UNITED STATES PATENT AND TRADEMARK OFFICE
CERTIFICATE OF CORRECTION

PATENT NO. : 7,098,305 B2  Page 1 of 1
APPLICATION NO. : 10/080130
DATED : August 29, 2006
INVENTOR(S) : Deghenghi et al.

It is certified that error appears in the above-identified patent and that said Letters Patent is hereby corrected as shown below:

Title Page:
Before Item (51), insert the following:
-- Related U.S. Application Data
--(60) Provisional application no. 60/317,616, filed on Sep. 6, 2001. --.

Column 2:
Line 36, change "Teverelix. for" to -- Teverelix for --.

Column 3:
Line 57, before "a GnRH antagonist)", change "Teverelix," to -- (Teverelix, --.

Column 5:
Line 62, change "$NH_2$.trifluoroacetate" to -- $NH_2$·trifluoroacetate --.

Column 6:
Line 3, change "$NH_2$.trifluoroacetate" to -- $NH_2$·trifluoroacetate --.
Line 31, change "$NH_2$.trifluoroacetate" to -- $NH_2$·trifluoroacetate --.
Line 44, change "$NH_2$.trifluoroacetate" to -- $NH_2$·trifluoroacetate --.
Line 55, change "$NH_2$.trifluoroacetate" to -- $NH_2$·trifluoroacetate --.
Line 58, change "$NH_2$.trifluoroacetate" to -- $NH_2$·trifluoroacetate --.

Signed and Sealed this

Fifth Day of December, 2006

JON W. DUDAS
*Director of the United States Patent and Trademark Office*